(12) United States Patent
Meyer et al.

(10) Patent No.: US 6,718,128 B2
(45) Date of Patent: Apr. 6, 2004

(54) RADIANT WARMER WITH DISTANCE DETERMINATION BETWEEN HEATER AND PATIENT

(75) Inventors: Irwin Joseph Meyer, Auckland (NZ); Andrew Paul Maxwell Salmon, Auckland (NZ); Tak-Ming Chung, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 09/891,646

(22) Filed: Jun. 26, 2001

(65) Prior Publication Data

US 2002/0018648 A1 Feb. 14, 2002

(30) Foreign Application Priority Data

| Jun. 28, 2000 | (NZ) | ................................. 505466 |
| Jul. 26, 2000 | (NZ) | ................................. 506003 |
| Apr. 26, 2001 | (NZ) | ................................. 511375 |

(51) Int. Cl.$^7$ ................................. F26B 3/30
(52) U.S. Cl. .................. 392/418; 392/412; 607/96; 607/88
(58) Field of Search ................ 392/418, 407, 392/416, 412–413, 415; 219/506, 490, 518, 217, 521; 600/22; 607/88, 96, 100, 108–112; 250/494.1, 495.1, 493.1

(56) References Cited

U.S. PATENT DOCUMENTS

| 2,681,061 | A | * | 6/1954 | Modell ........................ 392/412 |
| 3,023,398 | A | | 2/1962 | Siegert |
| 3,338,233 | A | * | 8/1967 | Grosholz et al. |
| 3,433,953 | A | | 3/1969 | Sweet et al. |
| 3,444,739 | A | | 5/1969 | Treharne |
| 3,610,931 | A | | 10/1971 | Woolfson |
| 3,745,360 | A | | 7/1973 | Paul |
| 3,768,059 | A | | 10/1973 | Day |
| 4,621,615 | A | | 11/1986 | McGee |
| 4,832,029 | A | * | 5/1989 | Koch et al. .................. 607/100 |
| 4,833,304 | A | * | 5/1989 | Ueda .......................... 219/518 |
| 5,162,038 | A | * | 11/1992 | Wilker ......................... 600/22 |
| 5,163,323 | A | * | 11/1992 | Davidson ................... 73/290 V |
| 5,231,770 | A | * | 8/1993 | Fertig ........................... 34/266 |
| 5,335,308 | A | * | 8/1994 | Sorensen .................... 392/412 |
| 5,450,066 | A | | 9/1995 | Brighenti et al. |
| 5,511,322 | A | * | 4/1996 | Fertig ............................. 34/97 |
| 5,560,121 | A | * | 10/1996 | Fertig et al. .................... 34/90 |
| 5,798,503 | A | * | 8/1998 | Kersten et al. ............. 219/497 |
| 5,817,003 | A | * | 10/1998 | Moll et al. ..................... 600/22 |
| 5,841,944 | A | | 11/1998 | Hutchinson et al. |
| 6,015,234 | A | | 1/2000 | Gourrier et al. |
| 6,129,673 | A | | 10/2000 | Fraden |
| 6,226,454 | B1 | * | 5/2001 | Couture ...................... 392/415 |
| 6,294,758 | B1 | * | 9/2001 | Masao et al. ................ 219/553 |
| 6,296,606 | B1 | * | 10/2001 | Goldberg et al. ............. 600/22 |

FOREIGN PATENT DOCUMENTS

| EP | 851193 | * | 7/1998 |
| GB | 2282221 | | 3/1995 |
| GB | 2306210 | * | 4/1997 |
| WO | 9938429 | * | 8/1999 |

* cited by examiner

*Primary Examiner*—John A. Jeffery
(74) *Attorney, Agent, or Firm*—Trexler, Bushnell, Giangiorgi, Blackstone & Marr, Ltd.

(57) ABSTRACT

A system for heating a patient using a radiant heater is disclosed. In order to ensure optimum positioning of the patient various location and indication embodiments are included. The present invention either adjusts the energization of the heater to provide optimum heating, provides an indicator of the optimum position for the patient, indicates that the patient is not correctly positioned or any combination thereof.

47 Claims, 10 Drawing Sheets

RADIANT WARMER WITH DISTANCE DETERMINATION BETWEEN HEATER AND PATIENT

FIELD OF THE INVENTION

The present invention relates to the use of apparatus for heating a patient particularly although not solely for optimum location of a patient in relation to a radiant warmer.

BACKGROUND ART

One method of warming patients during surgical procedures is to use a radiant warmer positioned above the patient's head or other body parts having good blood perfusion for example. For example, in our U.S. Pat. No. 5,841,944 we describe an apparatus for supporting and heating an infant using an infrared radiant heater, Typically the radiant heater will have a reflector such that the infrared radiation emitted by the heater will have a relatively narrow beam.

The problem with this method of warming can be positioning the patient relative to the heater element to ensure that enough, but not too much, power is delivered. Another difficulty is knowing how well perfused the skin is, under the warmer.

One way of achieving this in prior art devices is by indicating the height using a tape measure or other measure of distance to attempt to get the optimum level of radiation. This does not allow for inadvertent low or high settings when beds are raised or lowered or accidental heater movement during procedures. Then the patient is manually positioned laterally to a point where the surgical team estimate the radiation beam is roughly the target heating area.

It would therefore be desirable to have a radiant warmer in which it was easy to locate the patient directly in the path of the radiation focussed from the radiant heater. It would also be desirable to ensure that the patient is located at the optimum distance from the radiant heater in order to ensure that the correct level of heating is achieved.

SUMMARY OF THE INVENTION

It is therefore an object of the present invention to provide a system for heating a patient which goes some way to achieving the abovementioned desiderata, or which will at least provide the public or industry with a useful choice.

Accordingly in a first aspect the present invention consists in an apparatus for heating a patient, said patient in use supported by a surface, said apparatus comprising:
  a radiant heating means positioned at a distance from said patient,
  control means, adapted to either estimate or determine the location of said patient and depending on said location vary the energization of said radiant heating means or adapted to provide an indication of a predetermined location or provide indication of the absence of said patient in said predetermined location.

In a second aspect the present invention consists in an apparatus adapted to detect radiant heat energy incident on a surface comprising:
  a body portion; and
  at least two temperature sensing means wherein an unmasked temperature sensing means is located on a first side of said body portion and sensing means is located on the opposite side of said body portion.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in day sense limiting.

The invention consists in the foregoing and also envisages constructions of which the following gives examples.

BRIEF DESCRIPTION OF THE DRAWINGS

One preferred foam of the present invention will now be described with reference to the accompanying drawings in which.

DETAILED DESCRIPTION OF THE PREFERRED EMBODIMENT

The present invention is a system which ensures a patient receives the optimum benefit of heating from a radiant warmer. This is achieved by giving an audio/visual indication of whether or not the patient is located within the optimal heating zone. The optimal heating zone is characterised by the patient being at the optimal distance from the radiant heater as well as being positioned laterally in order to receive the correct amount of radiation available from the radiant warmer. This is achieved by providing two light sources which converge in the optimal heating zone or alternatively in a digital display which whether or not the patient is in the optimal heating zone and if not, gives directions as to where the patient should be moved to.

Figure 1:
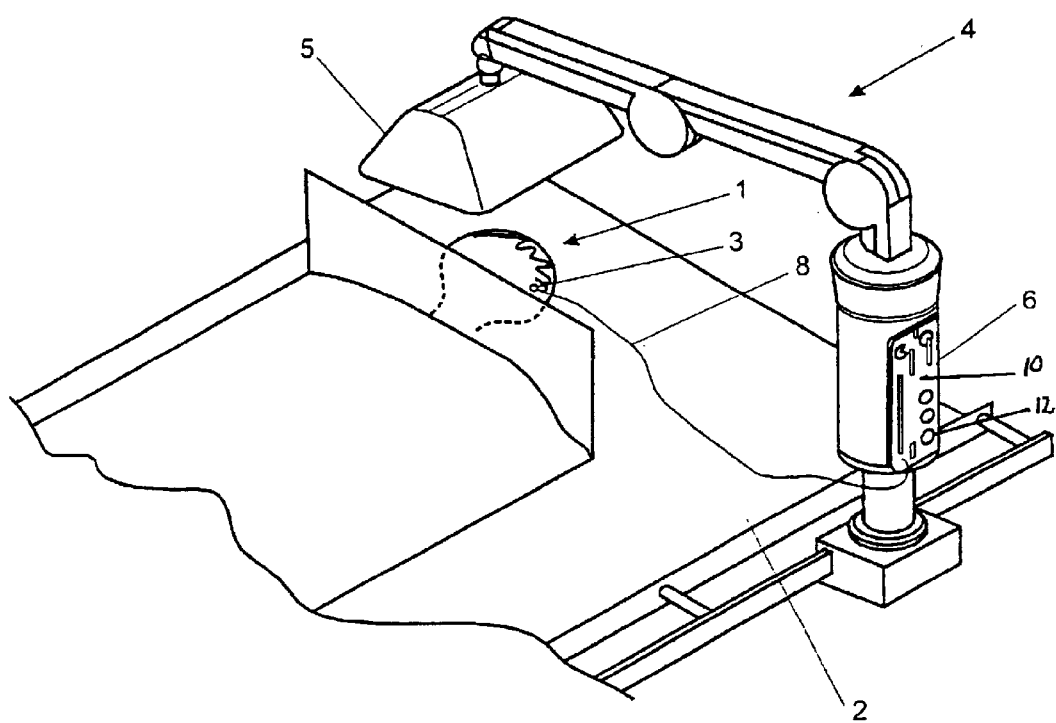
FIG. 1 is a illustration of a radiant heater in use according to the preferred embodiment of the present invention.

The present invention can be employed in any one of a number of applications, For example in FIG. 1 a radiant warmer is depicted for use in surgery. It includes a radiant heater head 5 supported by support columns 4. The infrared radiant energy is directed at the patient 1 on the bed 2. The radiant heater head 5 is adjustable in a number of directions to correctly direct the radiant energy at the patient. A temperature sensor 3 is placed on the patient's face to help ensure optimum heating, and is connected at 7 to the warmer controller 6.

Optical Positioning System

Figure 2:
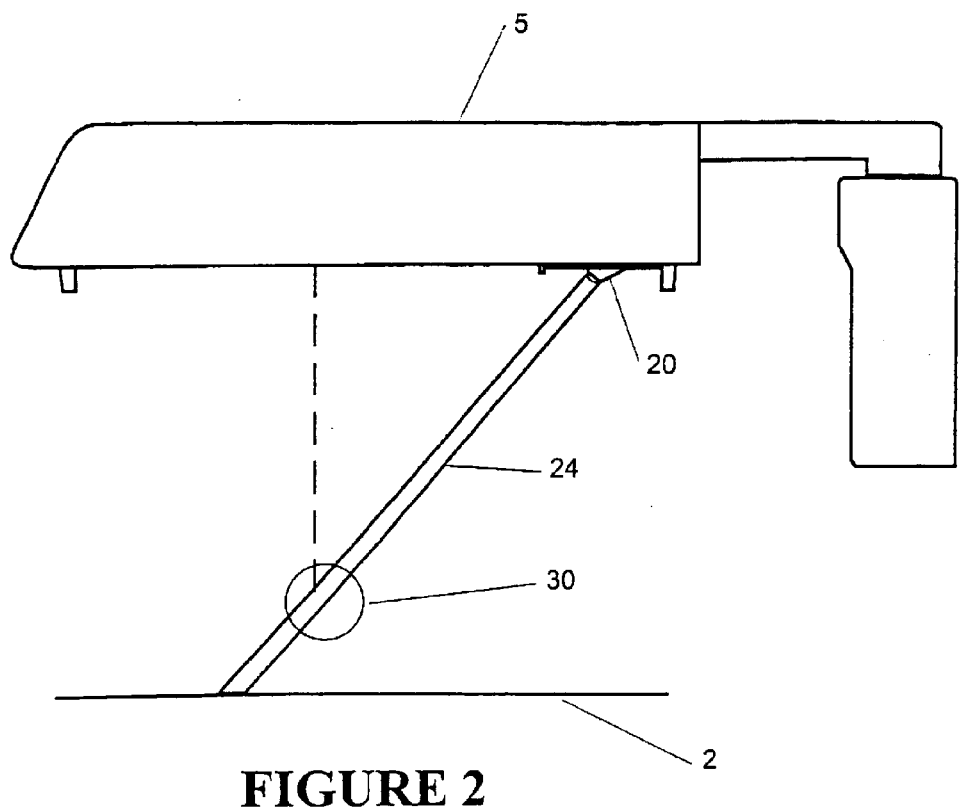
FIG. 2 is a side view of the operation of the preferred embodiment of the present invention.
Figure 3:
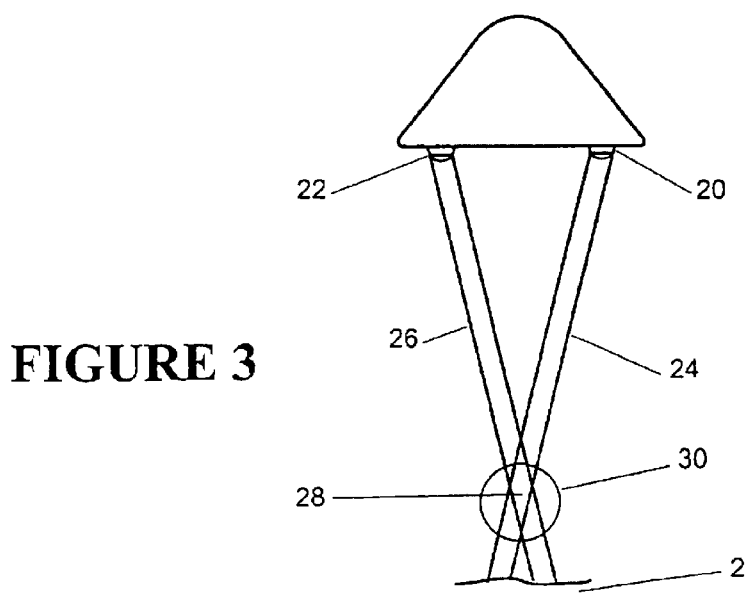
FIG. 3 is an end view of the operation of the preferred embodiment of the present invention.

In the preferred embodiment of the present invention shown in FIGS. 2 and 3, the warmer heater head unit 5 includes a first light source 20 and a second light source 22. Each light source provides a focus beam of visible light directed Generally down towards the bed 2 shown by a first dotted light path 24 and a second dotted light path 26 respectively.

Figure 5:
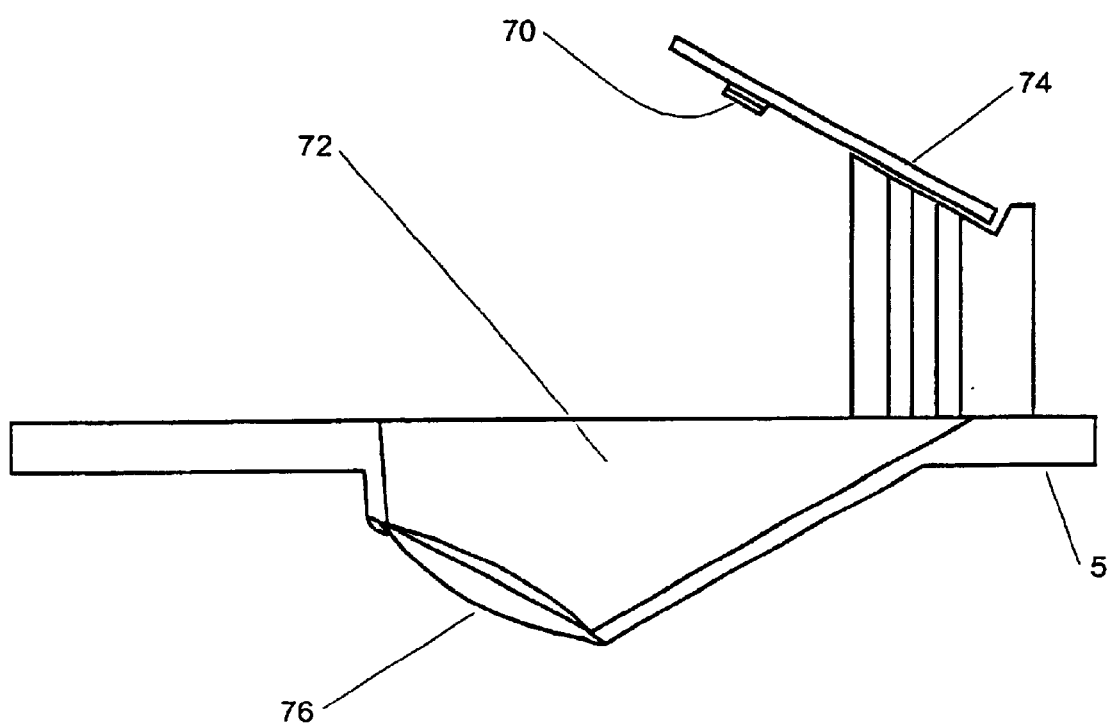
FIG. 5 is a cross section of a light source.

The first light source 20 and the second light source 22 may be provided by example using LEDs to provide the visible light together with an optical lens to focus the light. In each case the intensity of the light must be below a certain intensity in order to prevent any damage should the light be shone directly into the infant or patient's eyes. However it still needs to be bright enough to be clearly visible when shining against the patient or infant and therefore they are only energised intermittently. An example of a light source is shown in FIG. 5. An LED 70 mounted on a PCB 74 is positioned roughly above the centre of a cavity 72 with the heater head structure 5. The light emitted from the LED 70, is focussed by a lens 76 into a narrow beam of light.

As is seen in FIGS. 2 and 3 the first light path 24 and the second light path 26 converge in 3-dimensions at a single point 28. This point 28 is at the centre of an optimal heating zone 30 in which the patient should be positioned in order to provide optimal heating, accordingly by repositioning the patient it will be obvious whether it is necessary to raise or lower the heater head 5 or move the patient laterally in order to position the patient within proximity to this desired position.

Ultrasonic Patient Detector

Figure 4:
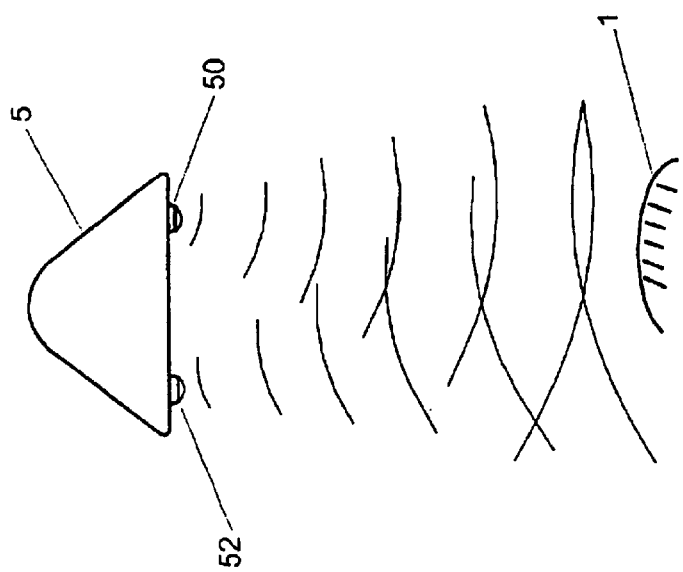
FIG. 4 is an end side view showing the operation of the ultrasonic method.

In an alternative embodiment shown in FIG. 4 the present invention is shown using an ultrasonic transmitter 50 and receiver 52 which is used in conjunction with the circuit shown in FIG. 7 to detect the distance to the object directly below the radiant heater head 5. This distance signal can then be used to provide the operator with a range of useful information. For example, if the patient 1 is under the radiant heater head 5 it can indicate to the user whether the radiant heater head is positioned at the correct height with respect to the patient. If there is an abrupt change in the distance detected by the ultrasonic transducer then this can also be indicated as the patient being moved or similar.

Figure 6:
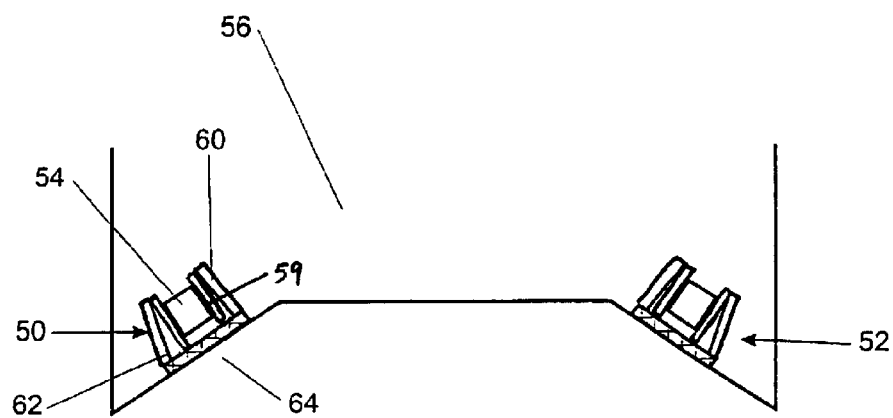
FIG. 6 is a cross section of the ultrasonic transmitter/receiver.

In FIG. 6 is shown the ultrasonic transducer housing (used for transmitter 50 and receiver 52) in detail. The transducer 54, being piezo electric or similar, is located within a cavity 56 in the heater head 5. The transducer 54 is housed in open ended cylindrical housing 60 and seated in a foam cylinder 59. The foam cylinder 59 provides acoustic insulation from the heater bead 5, to prevent the ultrasonic waves being conducted directly through the heater head 5. The housing 60 is attached at its base 62 to the interior of the cavity 56, and are directed at the centre of the bed 2 under the middle point of the radiant heater head 5 The front of the transducer 54 is covered by a perforated shield 64 to protect against damage.

In the preferred embodiment of the present invention the detected patient distance is used to control the radiant warmer power within a specified range. Where the patient is within 10–50 cm of the heater head, the radiant energy is controlled to ensure that the radiant power delivered to the patient is at safe and effective levels. If the patient is outside of the specified range the warmer will indicate that effective heating cannot be maintained and alert the user.

Figure 7:
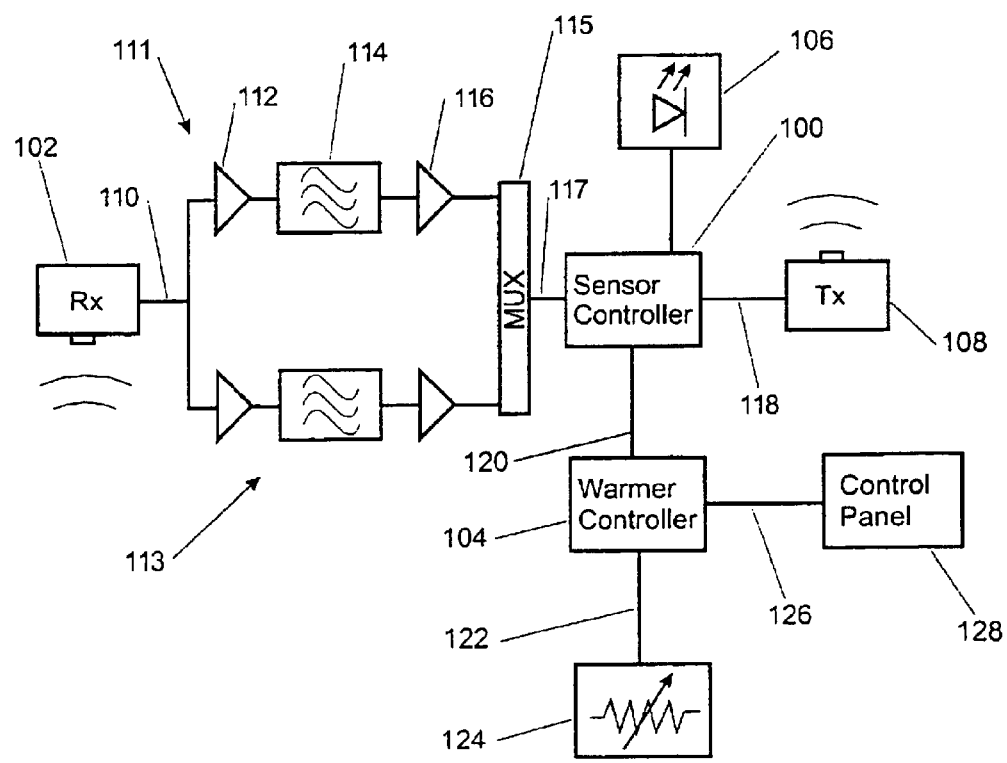
FIG. 7 is a block diagram of the circuit controlling the ultrasonic transducer

The ultrasonic transducer is part of the circuit shown in FIG. 7. The sensor controller 100 receivers as input the filtered output of the ultrasonic receiver 102, and provides as output signals to the warmer controller 104, the light source 106 and the ultrasonic transmitter 108. The raw output 110 from the receiver 102 is amplified 112, filtered 114 and amplified again 116 to provide a filtered signal 117 to the sensor controller 100. In order to give a wide dynamic range, several filtered amplification circuits are provided For example, the second circuit 113 has a different amplification level to the first circuit 111. The outputs 117 of both are feed to the controller 100, through multiplexer 115, which decides the most appropriate circuit to use. The control signal 118 to the transmitter 108 is in the range 25k–40 kHz, according to the capabilities of the particular transmitter. Thus the relationship between transmitted and received signals is analysed to estimate the distance to the patient. Once the patient is detected as being within the control zone, the light source 106 is temporarily energised to allow optimum lateral positioning. The control signals 120 to the warmer controller 104 relate to energization levels 122 for the radiant heater 124 and information 126 for the display panel 128. It will be appreciated that all functions could be implemented in a single digital processor or equally using analogue circuitry.

Figure 9:
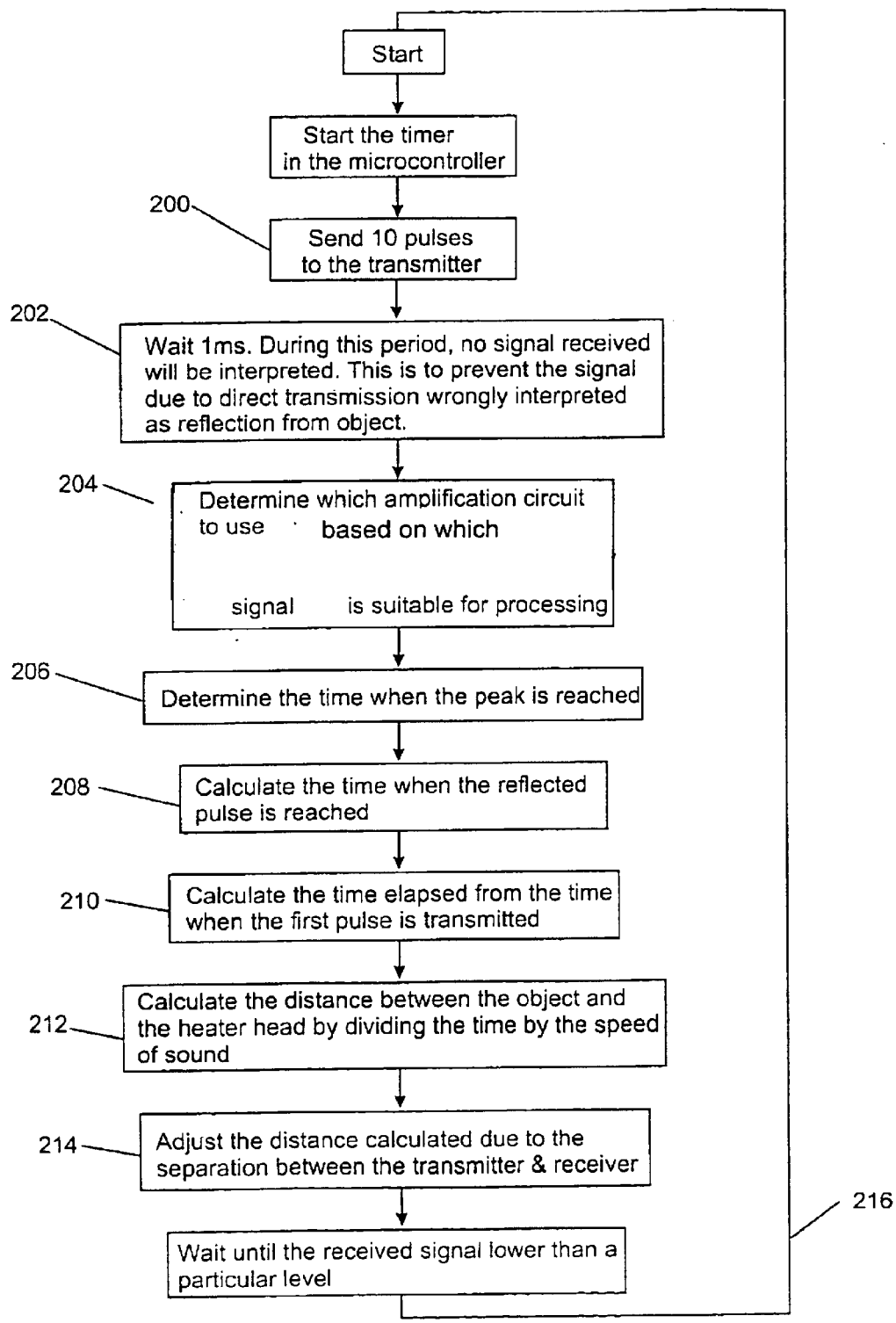
FIG. 9 is a flow diagram of the distance calculation algorithm.

Referring now to FIG. 9, the control strategy is shown for calculating the distance to the patient. Firstly the transmitter is instructed 200 to send 10 pulses. The controller pauses 202 for 1 ms, whereupon the outputs of the various filtered amplification circuits are queried 204 to choose an appropriate circuit (based on output level being within a range).

Figure 10:
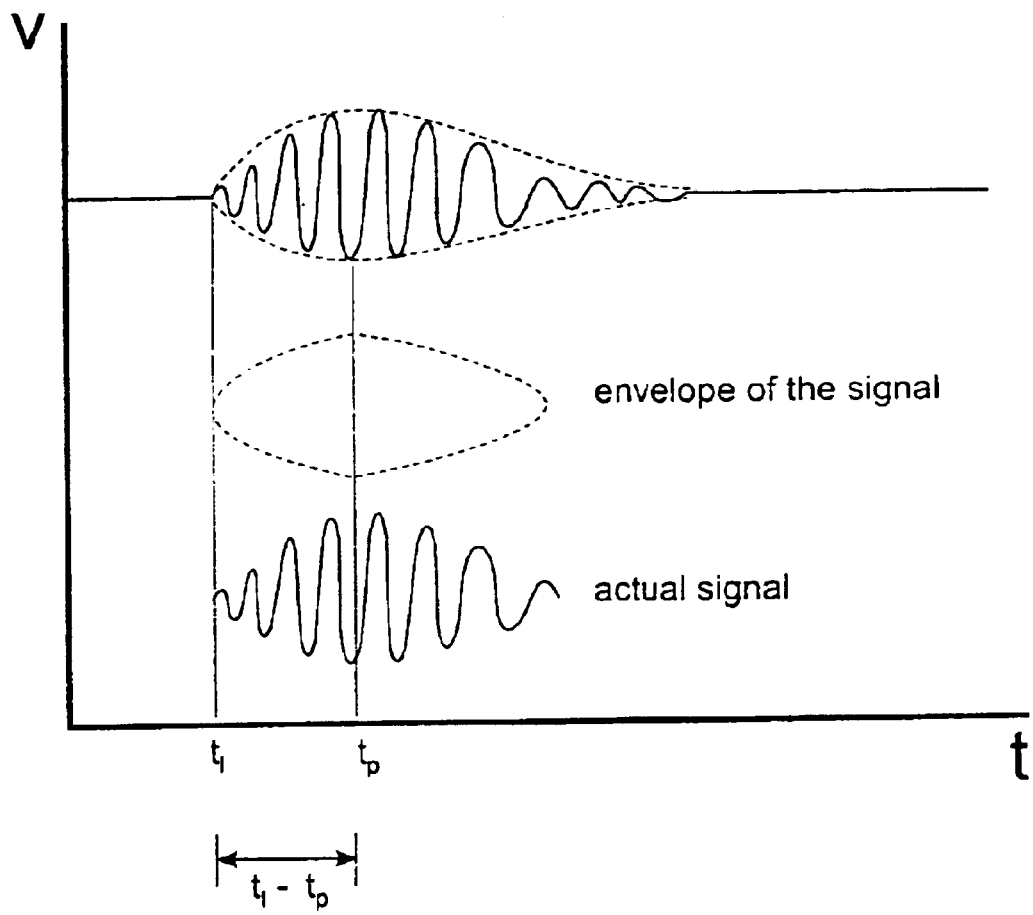
FIG. 10 is a graph of a typical received ultrasonic signal.

In FIG. 10 an example of the received signal is shown. The time $t_f$, when the first pulse is received is hard to measure as the amplitude is low. However, the peak time $t_p$ when the peak amplitide is reached is easily measured. Moreover as the time $t_{f-p}$ between the first pulse received $t_f$ and the peak $t_p$ is a constant, and owing $t_p$, $t_f$ can be easily calculated.

Thus again referring to FIG. 9 the next step is to record $t_p$ 206, and calculate $t_f$, 208. Thus the time between the first transmitted and first received pulse can be calculated 210. The distance is calculated 212 by dividing the time by the speed of sound, and this is adjusted 219 due to the separation between Tx and Rx. This process loops continually 216 to constantly measure distance.

Figure 8:
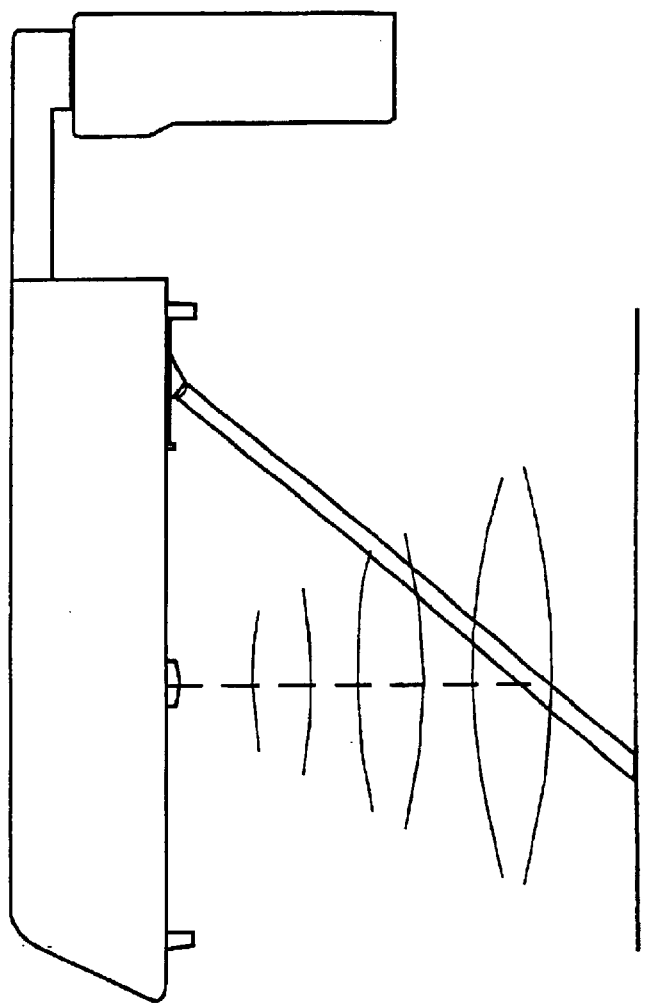
FIG. 8 is a side view of the combined optical ultrasonic system.

In a further improvement the ultrasonic transducer 50 could be combined with a single light source directed to the centre of the heating zones, as shown in FIG. 8. This gives a visual indication if the warmer is correctly laterally positioned as well as the automatic control over the level of radiation allowed by the ultrasonic transducer. Further the light source could be provided with a lens (not shown), with a focal point coinciding with the optimal heating zone. In this configuration the user knows the unit/patient are correctly positioned when the light is perfectly focussed on the desired heating zone on the patient.

Radiant Energy Sensor

The previously described sensor 3 is now improved upon as follows. We have found that by using two standard thermistor temperature measurement beads one on top of the other, with a thermally resistive material between them, we can detect changes in energy delivered to the sensor. At the same time we can accurately measure skin temperature.

This means that we can safely limit and ensure adequate temperature energy to the patient regardless of heater-patient distance by limiting the power delivered according to energy level. Also if the heater unit is incorrectly positioned to deliver sufficient energy we can alert the user, so that the heater or patient can be repositioned.

Another benefit of using this type of sensor is being able to measure heat flux, or the flow of energy into the skin. This measurement allows the warmer to compensate for low perfused body surfaces by reducing the temperature and energy on this surface.

Figure 11:
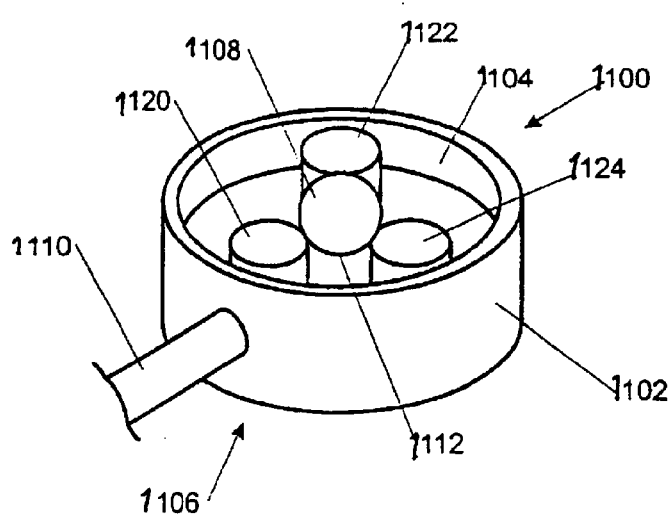
FIG. 11 is a cross-section of the sensor construction according to the preferred embodiment of the present invention.
Figure 12:
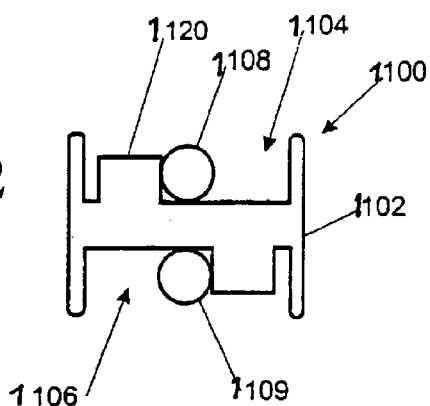
FIG. 12 is a perspective view of the sensor construction according to the preferred embodiment of the present invention.

Referring now to FIG. 11, the basic construction of the sensor 1100 is shown in cross-section. The body portion 1102 is effectively a disk with cavities 1104, 1106 on either end. Contained in upper cavity 1104 is a thermistor bead 1108 to which external electrical connection 1110 is made through connectors 1112. Also, as can be seen in FIG. 3, the thermistor bead 108 is also surrounded by support structures 1120, 1122, 1124 in order to keep the thermistor bead in the correct position and protect it from damage. It will be appreciated that the construction in the upper cavity 1104 and the lower cavity 1106 are essentially identical with an identical bead 1109 in lower cavity 1106.

Figure 13:
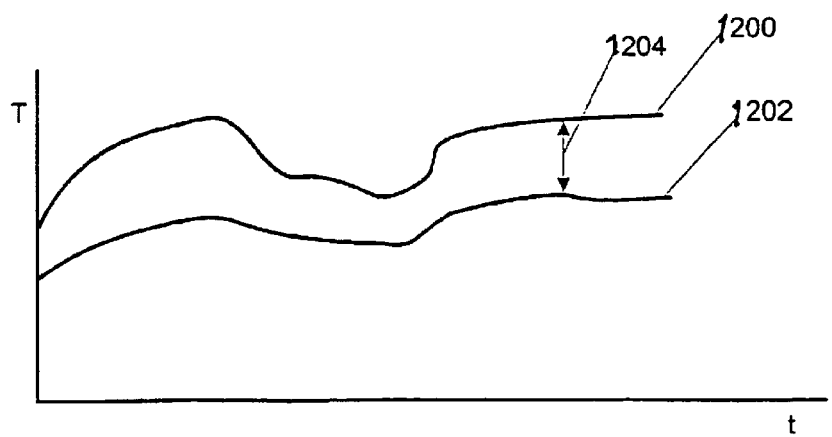
FIG. 13 is a graph indicating the typical profiles of the temperature measured by each thermistor according to the preferred embodiment of the present invention.

Referring now to FIG. 13, a graph of the typical temperature profile is shown for each sensor when the sensor 1100 (3, FIG. 1) and heater head (5, FIG. 1) are correctly positioned. The top trace 1200 represents the upper thermistor 1108 which is exposed to the radiation. The lower trace 1202 represents the lower thermistor 1109 which is masked from the radiation by the body portion. Effectively, the bottom profile 1202 is a measure of the skin temperature of the patient. The upper profile 1200 therefore represents the temperature of a nominal surface with no heat absorption capability. Thus, the difference 1204 in these two temperatures represents a measure of the level of radiant heat energy being absorbed by the patient's skin. An empirically derived relationship can be used to indicate whether the heater head is delivering adequate radiation, and therefore correctly positioned. A temperature difference of the order of greater than ½° C. is a reasonable indication of correct positioning.

As shown in FIG. 1 where the controller 6 detects a temperature difference below ½° C., it provides an alarm signal to the display panel 10 The heater head 5 attached to adjustable mounting arm 4 may then be repositioned accordingly. Controller 6 may also control energization of heater head 5 to give a desired skin temperature, by control dial 12, and measured by lower bead 1109.

Figure 14:
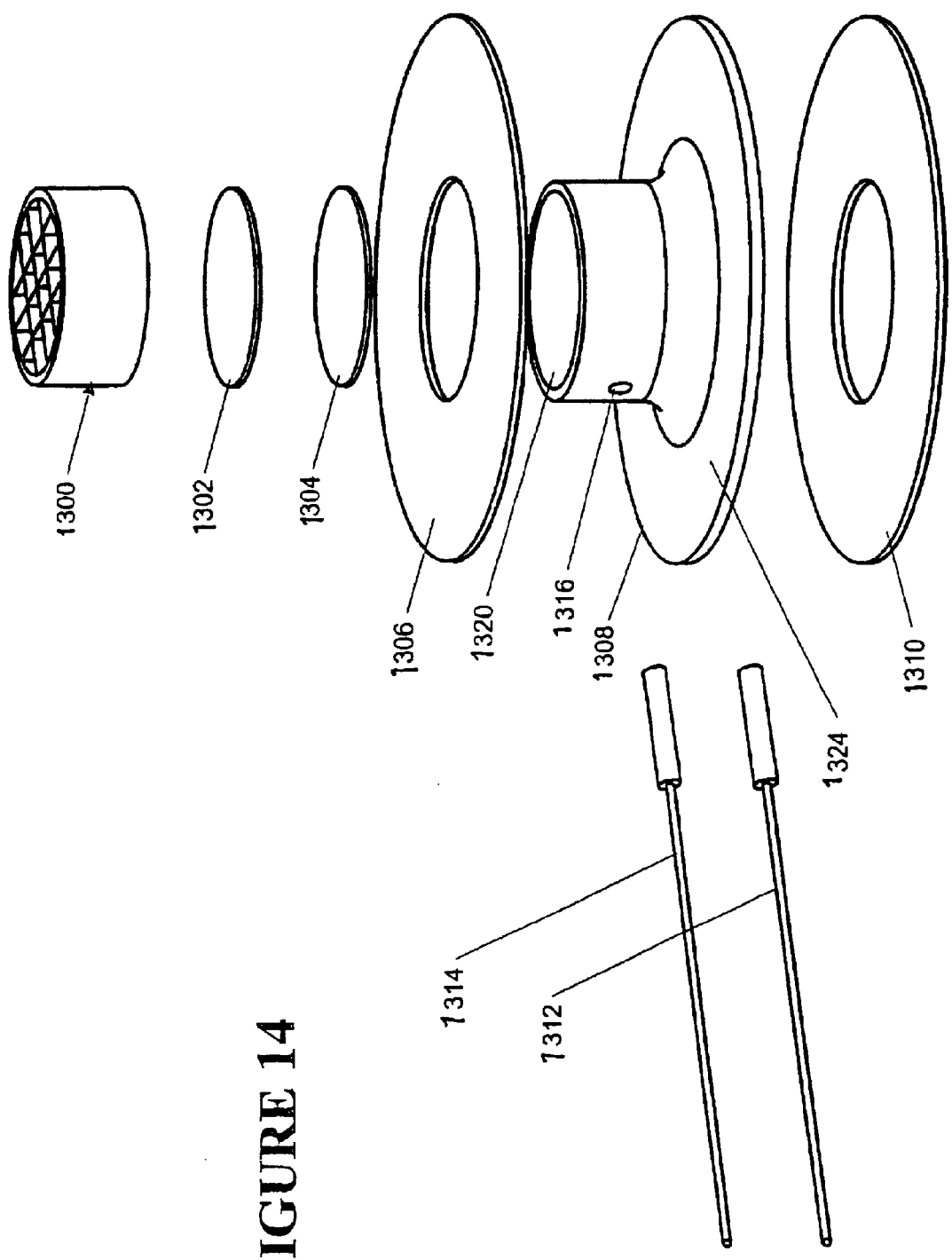
FIG. 14 is a blown out perspective view of a further embodiment of the sensor.
Figure 15:
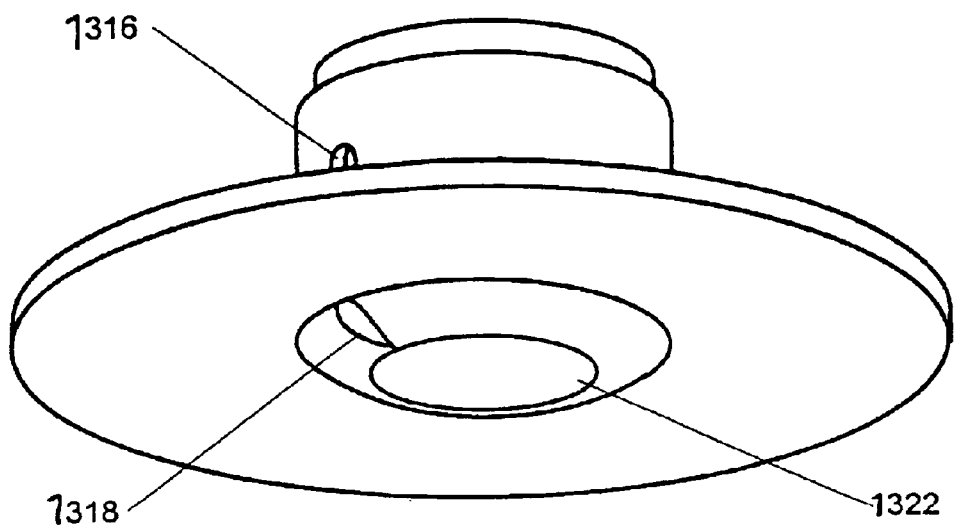
FIG. 15 is a perspective view of a further embodiment of the sensor from underneath.
Figure 16:
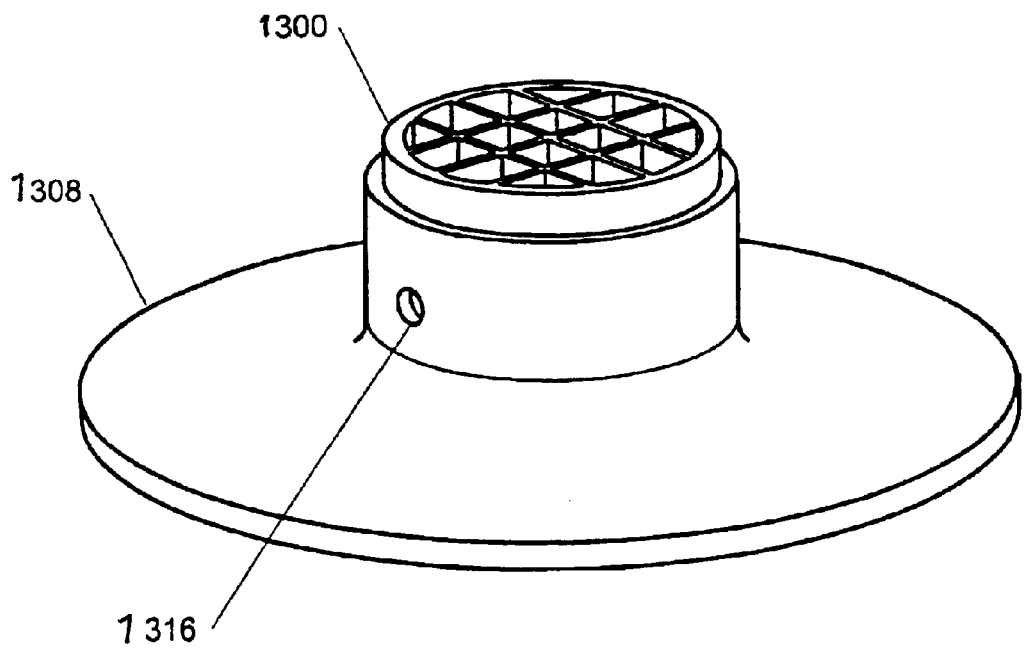
FIG. 16 is a perspective view of a further embodiment of the sensor from above.

In a further embodiment shown in FIGS. 14 to 16 the present invention is illustrated in a form suitable for a disposable skin sensor. The sensor base 1308 is preferably constructed of a rigid material for example polyethylene or polypropylene. It includes an upper cylindrical cavity 1320, a lower cylindrical cavity 1322 and an annular flange 1324 of greater diameter between the two. The annular disk 1324 also provides thermal insulation (may be double layered in the centre with an air gap) between the upper cavity 1320 and the lower cavity 1322.

A disk 1304 of Nomax or other high efficiency insulation is inserted at the bottom of the upper cavity 1320. The Nomex is provided to ensure her insulation between the upper and lower cavities. On top of the Nomex is a disk 1302 of black copper which is provided to give a thermal mass for the upper cavity, and which also has a high emissivity in order to heat up quickly. The upper thermistor 1314 is inserted through aperture 1316 in the sensor base 1308 and sits on top of the disk 1302 of black copper. It is therefore in thermal conduct with the black copper and detects the temperature thereof. A sensor insert 1300 then sits on top of the upper thermistor 1314 which has a number of narrow vertical channels which allow vertical radiation but prevent or restrict any air currents to prevent convective losses from the black copper and top thermistor.

On the outer section of the annular disk 1324, on the top side thereof a reflective sheet is provided to reflect any thermal radiation from the areas of skin surrounding the sensor in order to provide a more accurate measure of skin temperature. On the underside of the annular disk 1324 is an adhesive base 1310 which is provided to attach the sensor to the skin of the patient.

The lower thermistor 1312 is inserted through an aperture 1318 in the lower cavity 1322 such that once in the lower cavity it is in close thermal contact with the patients' skin. The attachment of the adhesive base to the skin provides additional compressive force on the lower thermistor 1318 to the patient.

This further embodiment provides improved resolution of the level of thermal radiation. It will be appreciated by one skilled in the art that the integration of this further embodiment in the system as described in the preceding embodiment is equally possible to achieve the objects of the invention.

It will be appreciated in the foregoing that the concept of using the present invention as equally applicable to radiant warming in general and is not limited specifically to infant warning or patient warming during surgery. Similarly it will be appreciated that while the embodiments of the optical locator, ultrasonic detector, and/or sensor may be used independently it will also be obvious that the two could be combined as shown in FIG. 8 to provide a further embodiment of the present invention for optimally locating a patient for a radiant warmer.

The present invention which has been so described provides a number of advantages over the prior art, namely:

it allows easy location of a patient to provide optimal and safe warming it is simple and cheap to manufacture

What is claimed is:

1. An apparatus for heating a patient, said patient in use supported by a surface, said apparatus comprising:

a radiant heater positioned at a distance from said patient, indicator means configured to produce a zone of visible light radiation, said zone coinciding with an optimal heating zone in relation to said radiant heater, said zone of visible light radiation acting, for an observer, as an external indication on things placed within the zone of the location of optimal heating effect from said radiant heater, and a controller configured to estimate or determine the distance to said patient from said radiant heater, and if said distance is within a predetermined range, energising said radiant heater to a specific level, said specific level being related to said location.

2. An apparatus for heating a patient as claimed in claim 1 wherein said a radiant heater comprises a heating element which when energised emits infrared radiation and an infrared reflector which focuses the radiation emitted by said radiant heater.

3. An apparatus for heating a patient as claimed in claim 2 wherein said predetermined heating zone location relates to the optimum positioning of said patient relative to said radiant heater.

4. An apparatus for heating a patient as claimed in claim 3 wherein said controller comprises:
   detector means juxtaposed adjacent said radiant heater and adapted to provide an output signal indicative of the distance from said detector means to said patient,
   wherein said controller receives said output signal and adapted to energise said radiant heater to radiate an appropriate level of radiation for said distance or, if said patient is not within a predetermined range of distances, provides an audio and/or visual alert to the user that the patient is not located within said desired range.

5. An apparatus for heating a patient as claimed in claim 4 wherein said indicator means further comprises a visual indicator of said predetermined heating zone.

6. An apparatus for heating a patient as claimed in claim 5 wherein said indicator means further comprises:
   a first light source attached to said radiant heater directed generally at said predetermined heating zone, and
   a second light source attached to said radiant heater and generally directed at said predetermined heating zone;
   wherein the point at which a first light beam emitted from said first light source and a second light beam emitted from said second light source converges is approximately said predetermined heating zone.

7. An apparatus for heating a patient as claimed in claim 4 wherein said detecting means includes at least one ultrasonic transducer.

8. An apparatus for heating a patient as claimed in claim 4 wherein said alert includes information about whether the said patient is too near, too far away, or optimally positioned from said radiant heater.

9. An apparatus for heating a patient as claimed in claim 4 wherein said detector means comprising:
   a transmitter adapted to convert a control signal to a sent ultrasonic pressure pulse;
   an ultrasonic receiver adapted to convert a received ultrasonic pressure pulse into a response signal;
   a processor adapted to:
      a) send a control signal to said transmitter to send at least one ultrasonic pulse,
      b) receive said response signal,
      c) estimate the distance to said patient based on the time between at least a portion of said control signal and at least a portion of said response signal.

10. An apparatus for heating a patient as claimed in claim 9 wherein said detector means further comprising at least one filtering and amplification circuit adapted to filter and amplify said response signal before being received by said processor.

11. An apparatus for heating a patient as claimed in claim 10 wherein said detector means comprising at least two said filtering and amplification circuits, whereby the multiplexed output of said at least two circuits is received by said processor, said processor selecting which of said circuits output to use based on the output voltage of each circuit.

12. An apparatus for heating a patient as claimed in claim 11 wherein the voltage output of each circuit in use being different, and said processor selecting one circuit based on its voltage output being within a predetermined range.

13. An apparatus for heating a patient as claimed in any one of claims 1 to 3 further comprising radiant heat sensing means in use in contact with said patient, and said controller receiving as input the output from said radiant heat sensing means and depending on said output of said radiant heat sensing means either adapted to vary the energization of said radiant heating means or adapted to provide indication of the location of said radiant heat sensing means in relation to said predetermined heating zone.

14. An apparatus for heating a patient as claimed in claim 13 wherein said radiant heat sensing means comprises:
   a body portion; and
   at least two temperature sensing means wherein an unmasked temperature sensing means is located on a first side of said body portion and a masked temperature sensing means is located on the opposite side of said body portion to said first side.

15. An apparatus for heating a patient as claimed in claim 14 wherein in use said opposite side facing towards said patient and said masked temperature sensing means is juxtaposed in contact with said patient thereby being masked from said radiant heat energy by said body portion.

16. An apparatus for heating a patient as claimed in claim 15 wherein, in use said first side facing away from said patient and said unmasked temperature sensing means is juxtaposed directly in the path of said radiant energy.

17. An apparatus for heating a patient as claimed in claim 16 wherein, said controller adapted to:
   i) calculate the difference in temperature between said masked temperature sensing means and said unmasked temperature sensing means and,
   ii) determine based of said difference temperature whether said radiant energy is below a predetermined value.

18. An apparatus for heating a patient as claimed in claim 17 wherein said masked and unmasked temperature sensing means are electronic thermistor devices.

19. An apparatus for heating a patient as claimed in claim 18 wherein said body portion is constructed of a thermally insulating material.

20. An apparatus for heating a patient as claimed in claim 17 wherein if in (ii) said radiant energy is determined to be below said predetermined value, said controller is adapted to provide indication that said patient is not correctly positioned in said predetermined location.

21. An apparatus for heating a patient, said patient in use supported by a surface, said apparatus comprising:
   a radiant heating means positioned at a distance from said patient,
   detector means juxtaposed adjacent said radiant heating means and adapted to provide an output signal indicative of the distance from said detector means to said patient wherein said detector means comprise:
      a transmitter adapted to convert a control signal to a sent ultrasonic pressure pulse;
      an ultrasonic receiver adapted to convert a received ultrasonic pressure pulse into a response signal;
      a processor adapted to:
         a) send a control signal to said transmitter to send at least one ultrasonic pulse,
         b) receive said response signal,
         c) estimate the distance to said patient based on the time between at least a portion said control signal and at least a portion of said response signal; and
      at least two filtering and amplification circuits, whereby the multiplexed output of said at least two circuits is received by said processor, said processor selecting which of said circuits output to use based on the output voltage of each circuit, and control means, receiving said output signal from said detector means and adapted to energise said radiant heating means to radiate an appropriate level of radiation for said distance or if said patient is not within a predetermined range of distances, provides an audio and/or visual alert to the user that the patient is not located within said desired range.

22. An apparatus for heating a patient as claimed in claim 21 wherein the voltage output of each circuit in use being different, and said processor selecting one circuit based on its voltage output being within a predetermined range.

23. An apparatus for heating a patient, said patient in use supported by a surface, said apparatus comprising:
a radiant heating means positioned at a distance from said patient,
radiant heat sensing means in use in contact with said patient comprising:
a body portion, and
at least two temperature sensing means wherein an unmasked temperature sensing means is located on a first side of said body portion and a masked temperature sensing means is located on the opposite side of said body portion to said first side, and
control means, receiving as input the output from said radiant heat sensing means and depending on said output of said radiant heat sensing means either adapted to vary the energization of said radiant heating means or adapted to provide indication of the location of said radiant heat sensing means in relation to said predetermined location.

24. An apparatus for heating a patient as claimed in claim 23 wherein in use said opposite side faces towards said patient and said masked temperature sensing means is juxtaposed in contact with said patient thereby being masked from said radiant heat energy by said body portion.

25. An apparatus for heating a patient as claimed in claim 24 wherein, in use said first side faces away from said patient and said unmasked temperature sensing means is juxtaposed directly in the path of said radiant energy.

26. An apparatus for heating a patient as claimed in claim 25 wherein, said control means adapted to:
i) calculate the difference in temperature between said masked temperature sensing means and said unmasked temperature sensing means and,
ii) determine based of said difference temperature whether said radiant energy is below a predetermined value.

27. An apparatus for heating a patient as claimed in claim 26 wherein said masked and unmasked temperature sensing means are electronic thermistor devices.

28. An apparatus for heating a patient as claimed in claim 27 wherein said body portion is constructed of a thermally insulating material.

29. An apparatus for heating a patient as claimed in claim 26 wherein if in (ii) said radiant energy is determined to be below said predetermined value, said control means is adapted to provide indication that said patient is not correctly positioned in said predetermined location.

30. A method of heating a patient supported by a surface comprising the steps of:
providing a radiant heater, having a heating element which when energised emits infrared radiation and an infrared reflector which focuses the radiation emitted by said heater element, positioned at a distance from said patient;
providing an external indication to an observer of the degree to which such patient is in a pre-determined heating zone related to the optimum positioning of said patient relative to said radiant heater;
varying the energization of said radiant heater to a specific level if said location is within a pre-determined range, said specific level being related to said location;
detecting the distance from said radiant heater to said patient using at least one ultrasonic transducer by;
a) sending at least one ultrasonic pulse, from said transducer,
b) receiving a reflected pulse,
c) filtering and amplifying said response signal to provide at least two filtered and amplified signals,
d) selecting one of said signals based on the voltage level thereof, and
e) estimating the distance to said patient based on time between at least a portion of said pulse and at least a portion of said selected signal, and
energising said radiant heater to radiate an appropriate level of radiation for said distance or, if said patient is not within a predetermined range of distances, providing an audio and/or visual alert to the user that the patient is not located within said desired range including information about whether the said patient is too near, too far away, or optimally positioned from said radiant heater.

31. A method of heating a patient as claimed in claim 30 wherein the voltage level of each signal in use being different, and said selecting based on voltage level being within a predetermined range.

32. A method of heating a patient supported by a surface comprising the steps of:
providing a radiant heater, having a heating element which when energised emits infrared radiation and an infrared reflector which focuses the radiation emitted by said heating element, positioned at a distance from said patient;
providing an external indication to an observer of the degree to which such patient is in a pre-determined heating zone related to the optimum positioning of said patient relative to said radiant heater;
varying the energization of said radiant heater to a specific level if said location is within a pre-determined range, said specific level being related to said location;
detecting the distance from said radiant heater to said patient, and
energising said radiant heater to radiate an appropriate level of radiation for said distance or, if said patient is not within a predetermined range of distances, providing an audio and/or visual alert to the user that the patient is not located within said desired range; and
said radiant heat sensing comprises sensing radiant heat incident on said patient using an unmasked temperature sensing means and a masked temperature sensing means, and either varying the energization of said radiant heater or providing an indication of the location of said radiant heat sensing means in relation to said predetermined heating zone.

33. A method of heating a patient as claimed in claim 32 wherein in use said masked temperature is of the skin of said patient which is masked from said radiant heat energy.

34. A method of heating a patient as claimed in claim 33 wherein, in use said unmasked temperature is directly in the path of said radiant energy.

35. A method of heating a patient as claimed in claim 34 further comprising the steps of:
i) calculating the difference in temperature between said masked temperature sensing means and said unmasked temperature sensing means and, ii) determining based of said difference temperature whether said radiant energy is below a predetermined value.

36. A method of heating a patient as claimed in claim 35 wherein said masked and unmasked temperature are sensed using electronic thermistor devices.

37. A method of heating a patient as claimed in claim 36 wherein said patient is masked by a thermally insulating material.

38. A method of heating a patient as claimed in claim 37 wherein if in (ii) said radiant energy is determined to be below said predetermined value, providing an indicating that said patient is not correctly positioned in said predetermined location.

39. An apparatus for heating a patient, said patient in use supported by a surface, said apparatus comprising:
 a radiant heater, having a heating element which when energised emits infrared radiation and an infrared reflector which focuses the radiation emitted by said heating element, positioned at a distance from said patient,
 indicator means configured to provide an external indication to an observer of the degree to which said patient is in a predetermined heating zone related to the optimum positioning of said patient relative to said radiant heater,
 a controller comprising:
  detector means juxtaposed adjacent said radiant heater and comprising:
   a transmitter adapted to convert a control signal to a sent ultrasonic pressure pulse;
   an ultrasonic receiver adapted to convert a received ultrasonic pressure pulse into a response signal;
   at least two said filtering and amplification circuits adapted to filter and amplify said response signal;
  a processor adapted to:
   a) send a control signal to said transmitter to send at least one ultrasonic pulse,
   b) receive the multiplexed outputs of said at least two circuits,
   c) select which of the outputs to use based on the output voltage of each circuit,
   d) estimate the distance to said patient based on the time between at least a portion of said control signal and at least a portion of said response signal, and
   e) provide an output signal indicative of the distance from said detector means to said patient,
 wherein said controller, based on said output signal, is adapted to energise said radiant heater to radiate an appropriate level of radiation for said distance or, if said patient is not within a predetermined range of distances, to provide an audio and/or visual alert to the user that the patient is not located within said desired range.

40. An apparatus for heating a patient as claimed in claim 39 wherein the voltage output of each circuit in use being different, and said processor selecting one circuit based on its voltage output being within a predetermined range.

41. An apparatus for heating a patient, said patient in use supported by a surface, said apparatus comprising:
 a radiant heater positioned at a distance from said patient;
 indicator means configured to provide an external indication to an observer of the degree to which said patient is in a predetermined heating zone in relation to said radiant heater;
 radiant heat sensing means in use in contact with said patient and providing an output, the radiant heat sensing means comprising a body portion and at least two temperature sensing means wherein an unmasked temperature sensing means is located on a first side of said body portion and a masked temperature sensing means is located on the opposite side of said body portion to said first side; and
 a controller configured to estimate or determine the location of said patient relative to said radiant heater, and if said location is within a predetermined range, energising said radiant heater to a specific level, said specific level being related to said location; and to receive as input the output from said radiant heat sensing means and depending on said output of said radiant heat sensing means either to vary the energization of said radiant heating means or provide indication of the location of said radiant heat sensing means in relation to said predetermined heating zone.

42. An apparatus for heating a patient as claimed in claim 41 wherein in use said opposite side facing towards said patient and said masked temperature sensing means is juxtaposed in contact with said patient thereby being masked from said radiant heat energy by said body portion.

43. An apparatus for heating a patient as claimed in claim 42 wherein, in use said first side facing away from said patient and said unmasked temperature sensing means is juxtaposed directly in the path of said radiant energy.

44. An apparatus for heating a patient as claimed in claim 43 wherein, said control means adapted to:
 i) calculate the difference in temperature between said masked temperature sensing means and said unmasked temperature sensing means and,
 ii) determine based of said difference temperature whether said radiant energy is below a predetermined value.

45. An apparatus for heating a patient as claimed in claim 44 wherein said masked and unmasked temperature sensing means are electronic thermistor devices.

46. An apparatus for heating a patient as claimed in claim 45 wherein said body portion is constructed of a thermally insulating material.

47. An apparatus for heating a patient as claimed in claim 44 wherein if in (ii) said radiant energy is determined to be below said predetermined value, said control means is adapted to provide indication that said patient is not correctly positioned in said predetermined location.

* * * * *

UNITED STATES PATENT AND TRADEMARK OFFICE
CERTIFICATE OF CORRECTION

PATENT NO. : 6,718,128 B2
DATED : April 6, 2004
INVENTOR(S) : Erwin Joseph Meyer, Andrew Paul Maxwell Salmon and Tak-Ming Chung It is certified that error appears in the above-identified patent and that said Letters Patent is hereby corrected as shown below:

Title page,
Item [75], Inventors, "Irwin Joseph Meyer" should be -- Erwin Joseph Meyer --

Column 2,
Line 7, "day" should be -- any --

Column 3
Line 61, "bead" should be -- head --

Column 4,
Line 16, "provided For" should be -- provided. For --
Line 44, "owing" should be -- knowing --

Column 6,
Line 34, "warning" should be -- warming --

Signed and Sealed this

Twenty-ninth Day of June, 2004

JON W. DUDAS
*Acting Director of the United States Patent and Trademark Office*